(12) United States Patent
Sato (10) Patent No.: US 10,980,499 B2
(45) Date of Patent: Apr. 20, 2021

(54) RADIATION-IRRADIATION SYSTEM

(71) Applicant: FUJIFILM CORPORATION, Tokyo (JP)

(72) Inventor: Masaru Sato, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 349 days.

(21) Appl. No.: 15/949,091

(22) Filed: Apr. 10, 2018

(65) Prior Publication Data

US 2018/0303444 A1 Oct. 25, 2018

(30) Foreign Application Priority Data

Apr. 25, 2017 (JP) .............................. JP2017-086706

(51) Int. Cl.
*A61B 6/00* (2006.01)
*A61B 6/10* (2006.01)
*A61B 6/06* (2006.01)

(52) U.S. Cl.
CPC .............. *A61B 6/4405* (2013.01); *A61B 6/06* (2013.01); *A61B 6/107* (2013.01); *A61B 6/40* (2013.01); *A61B 6/4411* (2013.01); *A61B 6/462* (2013.01); *A61B 6/465* (2013.01); *A61B 6/467* (2013.01); *A61B 6/542* (2013.01); *A61B 6/56* (2013.01); *A61B 6/566* (2013.01)

(58) Field of Classification Search
CPC .. A61B 6/06; A61B 6/107; A61B 6/40; A61B 6/4405; A61B 6/4411; A61B 6/462; A61B 6/465; A61B 6/467; A61B 6/542; A61B 5/56; A61B 6/566
See application file for complete search history.

(56) References Cited

U.S. PATENT DOCUMENTS

| | | | | |
|---|---|---|---|---|
| 5,077,771 A * | 12/1991 | Skillicorn | ................ | H05G 1/06 378/102 |
| 7,224,769 B2 * | 5/2007 | Turner | ..................... | A61B 6/14 378/102 |
| 7,329,046 B1 * | 2/2008 | Muszak | ............... | A61B 6/4441 378/196 |
| 7,684,544 B2 * | 3/2010 | Wilson | ................... | A61B 6/462 378/102 |
| 8,767,919 B2 * | 7/2014 | Nishino | ................ | A61B 6/488 378/108 |

(Continued)

FOREIGN PATENT DOCUMENTS

JP 2011-136022 A 7/2011

*Primary Examiner* — Dani Fox
*Assistant Examiner* — Soorena Kefayati
(74) *Attorney, Agent, or Firm* — Solaris Intellectual Property Group, PLLC (57) ABSTRACT

A radiation-irradiation system includes a radiation generating device that includes an exposure switch unit and a display device that includes a touch panel; the display device is adapted to be detachably mounted on the radiation generating device and displays an exposure switch mark on the touch panel; and an emission control unit validly receives only an irradiation instruction for radiation of the exposure switch unit in a case in which the display device is installed on the radiation generating device, and validly receives only an irradiation instruction for radiation of the exposure switch mark in the case of a state in which the display device is separated from the radiation generating device.

14 Claims, 4 Drawing Sheets

(56) References Cited

U.S. PATENT DOCUMENTS

| | | | | |
|---|---|---|---|---|
| 2011/0186741 A1* | 8/2011 | Ohta | | H05G 1/26 250/370.08 |
| 2011/0291800 A1* | 12/2011 | Butzine | | A61B 6/4405 340/8.1 |
| 2011/0293070 A1* | 12/2011 | Kamiya | | A61B 6/4405 378/102 |
| 2014/0205066 A1* | 7/2014 | Kitagawa | | A61B 6/542 378/62 |
| 2015/0055752 A1* | 2/2015 | Takahashi | | H04N 5/32 378/62 |
| 2015/0078528 A1* | 3/2015 | Okada | | H05G 1/44 378/97 |
| 2015/0085986 A1* | 3/2015 | Dinse | | A61B 6/10 378/98 |
| 2015/0098551 A1* | 4/2015 | Kwak | | A61B 6/587 378/91 |
| 2015/0164458 A1* | 6/2015 | Tajima | | H05G 1/44 378/97 |
| 2015/0164461 A1* | 6/2015 | Imamura | | H05G 1/44 378/97 |
| 2015/0350545 A1* | 12/2015 | Welsh | | A61B 6/462 348/77 |
| 2016/0029991 A1* | 2/2016 | Tajima | | A61B 6/461 378/98 |
| 2016/0058403 A1* | 3/2016 | Kim | | A61B 6/465 378/62 |
| 2016/0174918 A1* | 6/2016 | Wang | | A61B 6/588 378/63 |
| 2016/0183903 A1* | 6/2016 | Vandroux | | A61B 34/25 600/407 |
| 2016/0206261 A1* | 7/2016 | Lan | | A61B 6/4405 |
| 2017/0258434 A1* | 9/2017 | Koh | | A61B 6/545 |
| 2017/0290559 A1* | 10/2017 | Gemmel | | A61B 6/587 |
| 2017/0295336 A1* | 10/2017 | Kimura | | A61B 6/4233 |
| 2018/0028138 A1* | 2/2018 | Oh | | A61B 6/4464 |

* cited by examiner

RADIATION-IRRADIATION SYSTEM

CROSS REFERENCE TO RELATED APPLICATIONS

The present application claims priority under 35 U.S.C. § 119 to Japanese Patent Application No. 2017-086706 filed on Apr. 25, 2017. The above application is hereby expressly incorporated by reference, in its entirety, into the present application.

BACKGROUND

Technical Field

The present invention relates to a radiation-irradiation system that is used in radiography, and more particularly, to a portable radiation-irradiation system.

Related Art

Various portable (transportable) radiation-irradiation devices, which are used at home, in a disaster area, and the like, have been proposed in recent years.

For example, JP2011-136022A proposes a system that includes a portable radiation-irradiation device in which a radiation source is received, a cassette in which a radiation detector is received, and a personal digital assistant to which the radiation-irradiation device and the cassette are connected through cables.

Further, in the system disclosed in JP2011-136022A, radiation is emitted from the radiation-irradiation device by the operation of an exposure switch that is provided in the radiation-irradiation device.

However, in a case in which an irradiation instruction for radiation is performed by the exposure switch provided in the radiation-irradiation device as in the system disclosed in JP2011-136022A, the amount of radiation to be applied to a user, which performs the irradiation instruction, is increased.

SUMMARY

The invention has been made in consideration of the above-mentioned problem, and an object of the invention is to provide a radiation-irradiation system that can reduce amount of radiation to be applied to a user.

A first radiation-irradiation system of the invention comprises: a radiation generating device that includes a radiation generating unit for generating radiation, an emission control unit for controlling emission of the radiation, and an instruction receiving unit for receiving an irradiation instruction for the radiation; and a display device that includes a display unit. The radiation generating device and the display device include radio communication units that communicate with each other by radio, respectively; the display device is adapted to be detachably mounted on the radiation generating device, and displays an indicator, which receives an irradiation instruction for the radiation, on the display unit; the emission control unit validly receives only the irradiation instruction for the radiation of the instruction receiving unit between the irradiation instruction for the radiation of the instruction receiving unit and the irradiation instruction for the radiation of the indicator displayed on the display unit in a case in which the display device is installed on the radiation generating device; and the emission control unit validly receives only the irradiation instruction for the radiation of the indicator between the irradiation instruction for the radiation of the instruction receiving unit and the irradiation instruction for the radiation of the indicator displayed on the display unit in a case of a state in which the display device is separated from the radiation generating device.

A second radiation-irradiation system of the invention comprises: a radiation generating device that includes a radiation generating unit for generating radiation, an emission control unit for controlling emission of the radiation, and an instruction receiving unit for receiving an irradiation instruction for the radiation; and a display device that includes a display unit. The radiation generating device and the display device include radio communication units that communicate with each other by radio, respectively; the display device is adapted to be detachably mounted on the radiation generating device, and displays an indicator, which receives an irradiation instruction for the radiation, on the display unit; the emission control unit validly receives only the irradiation instruction for the radiation of the instruction receiving unit between the irradiation instruction for the radiation of the instruction receiving unit and the irradiation instruction for the radiation of the indicator displayed on the display unit in a case in which the display device is present in a range of a preset distance from the radiation generating device; and the emission control unit validly receives only the irradiation instruction for the radiation of the indicator between the irradiation instruction for the radiation of the instruction receiving unit and the irradiation instruction for the radiation of the indicator displayed on the display unit in a case in which the display device is present outside the range of the preset distance from the radiation generating device.

Further, in the first radiation-irradiation system of the invention, the display unit of the display device may display the indicator in the case of the state in which the display device is separated from the radiation generating device, and may not display the indicator in the case in which the display device is installed on the radiation generating device.

Furthermore, in the second radiation-irradiation system of the invention, the display unit of the display device may display the indicator in the case in which the display device is present outside the range of the preset distance from the radiation generating device, and may not display the indicator in the case in which the display device is present in the range of the preset distance from the radiation generating device.

Moreover, in the first and second radiation-irradiation systems of the invention, the radio communication unit of the display device may communicate with a radiation detector, which detects the radiation transmitted through a subject, by radio.

Further, in the first and second radiation-irradiation systems of the invention, the display device may output an accumulation start control signal for a detection signal of the radiation to the radiation detector according to emission of radiation from the radiation generating device.

Furthermore, in the first and second radiation-irradiation systems of the invention, it is preferable that the display unit of the display device is a touch panel.

Moreover, in the first and second radiation-irradiation systems of the invention, it is preferable that the display device is a tablet terminal.

Further, in the first and second radiation-irradiation systems of the invention, it is preferable that the display device is adapted to be detachably mounted on a surface of the radiation generating device opposite to an emission side of the radiation.

Furthermore, in the first and second radiation-irradiation systems of the invention, an installation member on which the display device is to be installed may be provided on the surface of the radiation generating device opposite to an emission side of the radiation.

Moreover, it is preferable that the first and second radiation-irradiation systems of the invention are transportable.

The first radiation-irradiation system of the invention includes the radiation generating device and the display device, and the display device is adapted to be detachably mounted on the radiation generating device and displays the indicator that receives an irradiation instruction for the radiation.

Further, only the irradiation instruction for the radiation of the instruction receiving unit of the radiation generating device is validly received in a case in which the display device is installed on the radiation generating device, and only the irradiation instruction for the radiation of the indicator displayed on the display device is validly received in a case of a state in which the display device is separated from the radiation generating device.

Since the display device is adapted to be separable from the radiation generating device as described above and the display device is allowed to display the indicator that receives the irradiation instruction for the radiation, a user can give an instruction to irradiate a subject with radiation by using the display device at a position away from the radiation generating device. Accordingly, it is possible to reduce the amount of radiation to be applied to the user.

Since only the irradiation instruction for the radiation of the instruction receiving unit of the radiation generating device is validly received in a case in which the display device is installed on the radiation generating device, it is possible to prevent the emission of radiation that is caused in a case in which the indicator displayed on the display device is operated by mistake.

The second radiation-irradiation system of the invention includes the radiation generating device and the display device, and the display device is adapted to be detachably mounted on the radiation generating device and displays the indicator that receives an irradiation instruction for the radiation.

Further, only the irradiation instruction for the radiation of the instruction receiving unit of the radiation generating device is validly received in a case in which the display device is present in the range of a preset distance from the radiation generating device, and only irradiation instruction for the radiation of the indicator displayed on the display device is validly received in a case in which the display device is present outside the range of the preset distance from the radiation generating device.

According to this structure, since a user can give an instruction to irradiate a subject with radiation by using the display device at a position away from the radiation generating device as in the first radiation-irradiation system, it is possible to reduce the amount of radiation to be applied to the user.

Since only the irradiation instruction for the radiation of the instruction receiving unit of the radiation generating device is validly received in a case in which the display device is present in the range of a preset distance from the radiation generating device, it is possible to prevent the emission of radiation that is caused in a case in which the indicator displayed on the display device is operated by mistake.

DETAILED DESCRIPTION

Figure 1:
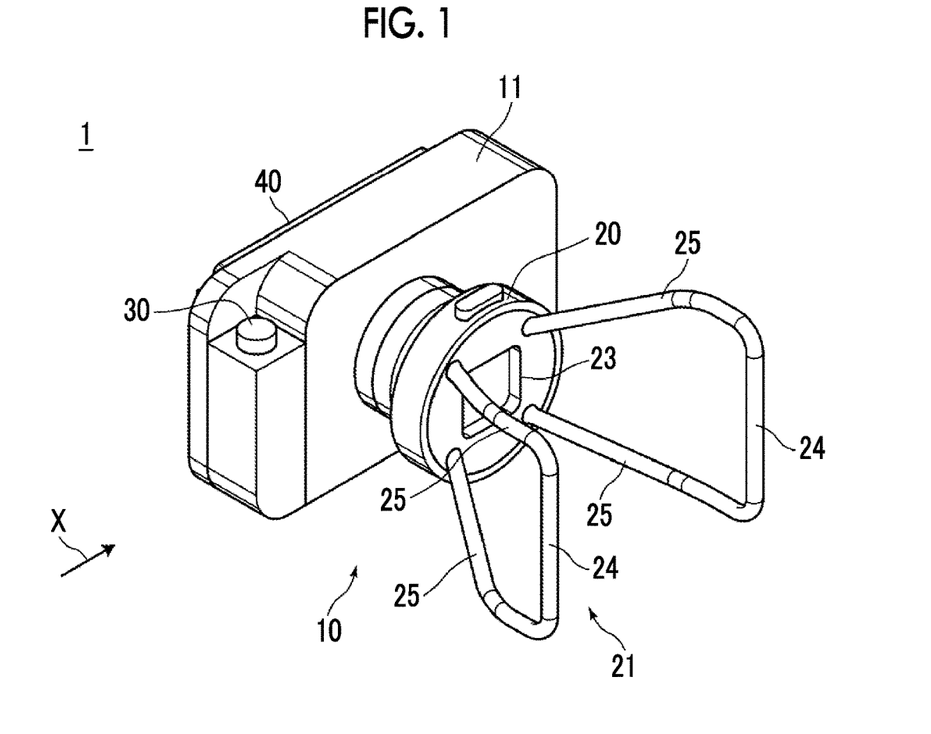
FIG. 1 is a perspective view showing the appearance of an embodiment of a radiation-irradiation system of the invention.
Figure 2:
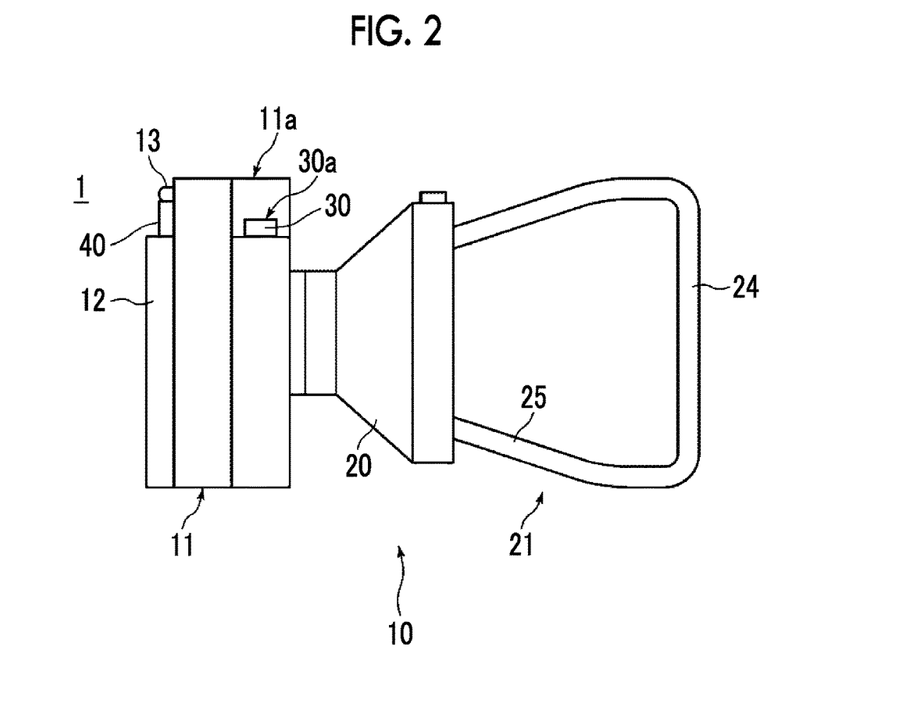
FIG. 2 is a diagram showing the side appearance of the radiation-irradiation system of FIG. 1 that is viewed in the direction of an arrow X.
Figure 3:
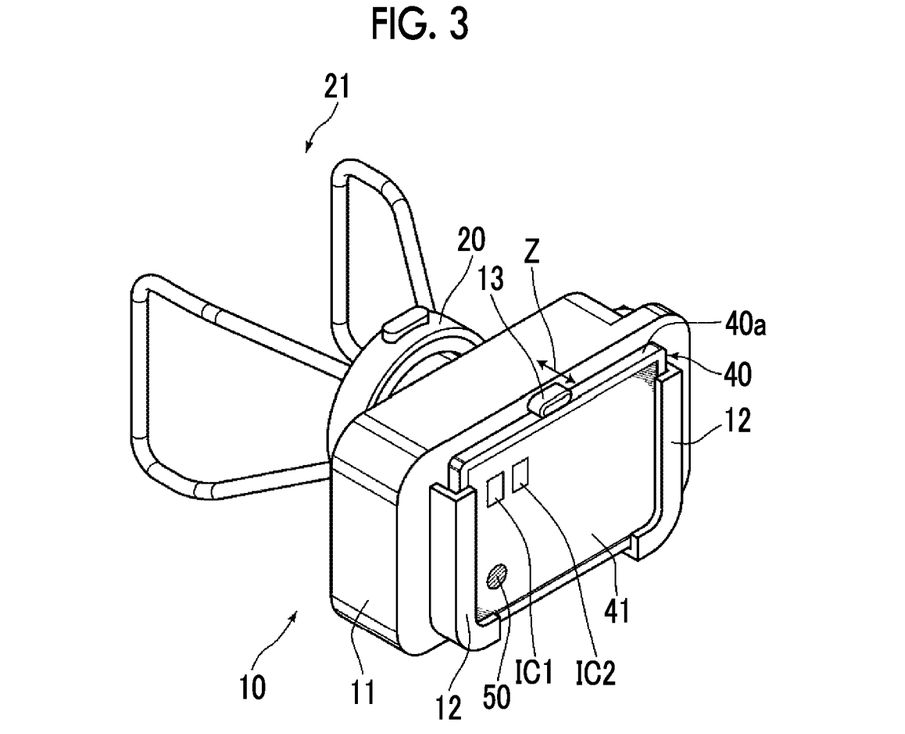
FIG. 3 is a diagram showing the appearance of the radiation-irradiation system of FIG. 1 from the back side.

A first embodiment of a radiation-irradiation system of the invention will be described in detail below with reference to the drawings. The radiation-irradiation system of this embodiment is a portable radiation-irradiation system that is mainly used at home, in a disaster area, and the like. FIG. 1 is a perspective view showing the appearance of the radiation-irradiation system 1 of this embodiment. Further, FIG. 2 is a diagram showing the side appearance of the radiation-irradiation system 1 of FIG. 1 that is viewed in the direction of an arrow X. Furthermore, FIG. 3 is a diagram showing the appearance of the radiation-irradiation system 1 of FIG. 1 from the back side. In this specification, the emission side of radiation of the radiation-irradiation system 1 is referred to as a front side, and the side of the radiation-irradiation system 1 opposite to the emission side of radiation is referred to as a back side.

As shown in FIGS. 1 to 3, the radiation-irradiation system 1 of this embodiment includes a radiation generating device 10 and a display device 40.

The radiation generating device 10 includes a radiation generating unit 11, a collimator unit 20, an interval ensuring unit 21, and an exposure switch unit 30 (corresponding to an instruction receiving unit of the invention).

The radiation generating unit 11 includes a radiation source 14 (see FIG. 5), such as an X-ray tube, which is provided in a housing and generates radiation, and emits radiation that is generated by the radiation source 14.

The collimator unit 20 controls the irradiation range for a patient that is to be irradiated with radiation generated by the radiation generating unit 11. The collimator unit 20 includes a diaphragm (not shown), and the irradiation range for the patient, which is to be irradiated with radiation, is controlled by a change in the size of the diaphragm. The size of the diaphragm is adapted to be capable of being manually changed by a user. Further, since the collimator unit 20 is provided with a rectangular emission port 23, radiation, which passes through the diaphragm, is emitted from the emission port 23.

As shown in FIGS. 1 and 2, the interval ensuring unit 21 includes contact members 24 and connection members 25. Each of the contact members 24 is a member that is in contact with a patient in a case in which a distance between the radiation generating unit 11 and the patient (subject) to be irradiated with radiation is shorter than a preset distance. An interval between the radiation generating unit 11 and the patient is ensured in a case in which the contact members 24 are in contact with the patient.

Four connection members 25 are provided around the emission port 23 of the collimator unit 20, and are members that extend from the collimator unit 20 in the emission direction of radiation. Further, the contact member 24 is provided between distal end portions of a set of two connection members 25. As shown in FIG. 1, the four connection members 25 are formed so that an interval between the connection members 25 is increased toward a patient from the collimator unit 20.

The exposure switch unit 30 receives an irradiation instruction for radiation. In a case in which the exposure switch unit 30 is pressed, radiation is emitted from the radiation generating device 10 and a patient is irradiated with the radiation. As shown in FIG. 1, the exposure switch unit 30 of this embodiment is provided at one corner of the housing of the radiation generating unit 11.

For the prevention of the exposure switch unit 30 being pressed by mistake, it is preferable that an upper surface 30a of the exposure switch unit 30 is positioned below an upper surface 11a of the housing of the radiation generating unit 11 as shown in FIG. 2.

Figure 4:
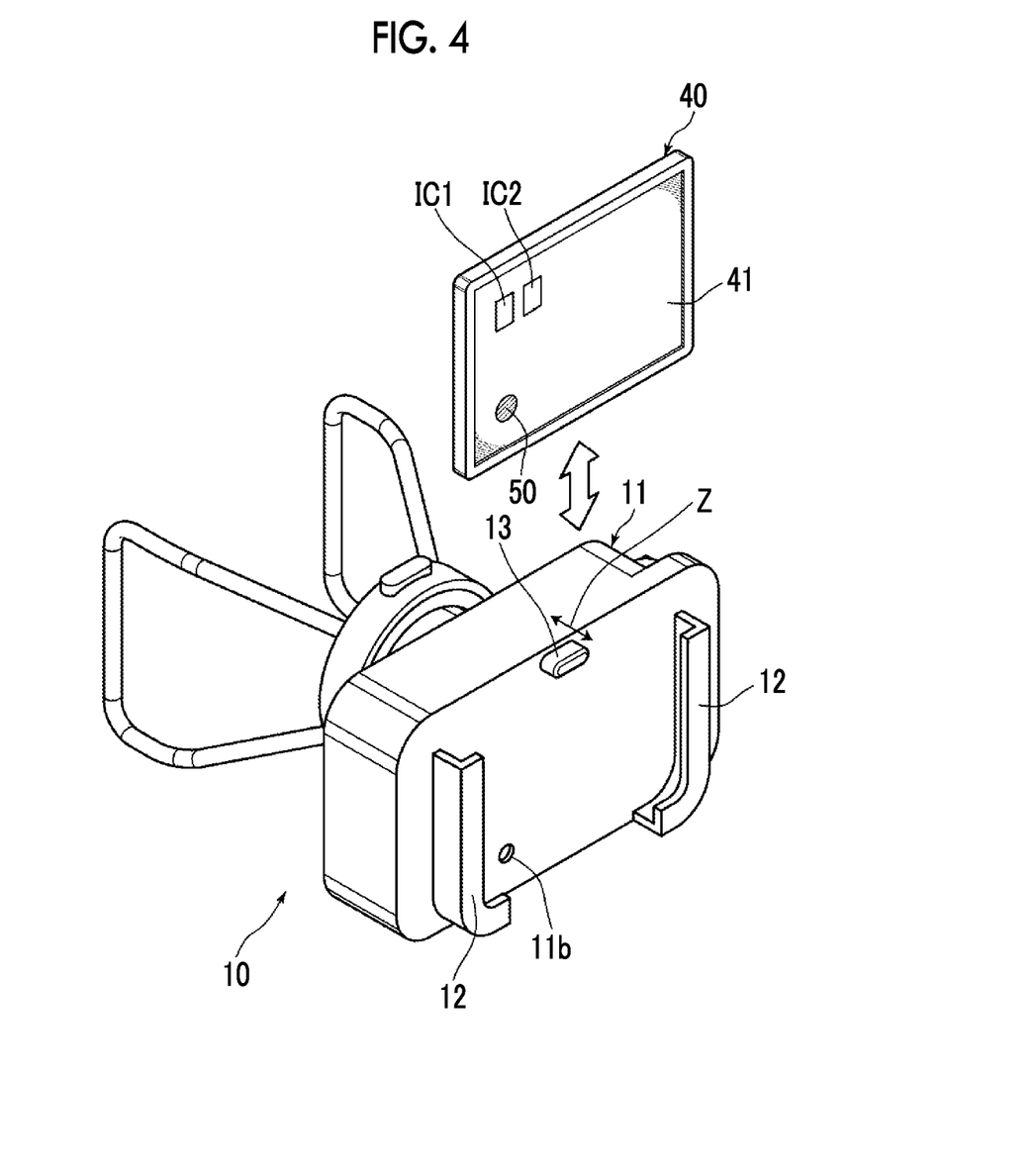
FIG. 4 is a diagram showing a state in which a display device is detached from a radiation generating device.

Further, installation members 12 on which the display device 40 is set are provided on the back side of the radiation generating unit 11 as shown in FIGS. 3 and 4. The installation members 12 are formed of two support members, and are adapted to support two sides of the display device 40 that are opposite to each other. FIG. 3 shows a state in which the display device 40 is installed on the installation members 12, and FIG. 4 shows a state in which the display device 40 is separated from the installation members 12 of the radiation generating unit 11.

Furthermore, a fixing member 13 is provided on the back of the radiation generating unit 11. The fixing member 13 is a member that is in contact with an upper end 40a of the display device 40 in a state in which the display device 40 is installed on the radiation generating unit 11. The display device 40 is supported by the installation members 12 and the position of the upper end 40a of the display device 40 is fixed by the fixing member 13, so that the display device 40 is fixed to the back of the radiation generating unit 11.

The fixing member 13 is adapted to be movable in the direction of an arrow Z shown in FIGS. 3 and 4, and is biased toward the outside of the housing of the radiation generating unit 11 by an elastic member, such as a spring. The fixing member 13 is adapted to protrude from the back of the radiation generating unit 11 as shown in FIGS. 3 and 4 in a state in which the fixing member 13 does not receive an external force, and is adapted to be pushed to the inside of the back of the radiation generating unit 11 in a state in which an external force is applied to the fixing member 13 inward in a Z direction (toward the front side from the back side). Further, the display device 40 is adapted to be separatable from the housing of the radiation generating unit 11 since the fixing member 13 is pushed as described above.

In this embodiment, the installation members 12 and the fixing member 13 are provided on the housing of the radiation generating unit 11 so that the display device 40 is adapted to be detachably mounted on the radiation generating unit 11. However, the invention is not limited thereto, and the display device 40 may be adapted to be detachably mounted on the radiation generating unit 11 by, for example, magnets. Further, a member having adhesiveness may be provided on each of the housing of the radiation generating unit 11 and a housing of the display device 40 so that the display device 40 is adapted to be detachably mounted on the radiation generating unit 11. A hook-and-loop fastener (for example, MAGIC TAPE (registered trademark)) may be used as the member having adhesiveness, and an adhesive tape having adhesiveness may be used as the member having adhesiveness.

Next, the display device 40 will be described. The display device 40 is formed of a tablet terminal that includes a touch panel 41 (corresponding to a display unit of the invention). Icons IC1 and IC2 of applications, which are installed in the display device 40, are displayed on the touch panel 41 of the display device 40. Only two icons IC1 and IC2 are displayed in FIGS. 3 and 4, but the number of the installed applications is not limited to two, and three or more applications may be installed.

Further, the display device 40 displays an exposure switch mark 50 (corresponding to an indicator of the invention) that receives an irradiation instruction for radiation. In a case in which the exposure switch mark 50 is touched by a user in a state in which the display device 40 is separated from the radiation generating device 10, radiation is emitted from the radiation generating device 10.

Furthermore, a control program, which controls the operation of the radiation generating device 10 and the operation of a radiation detecting device 60 (see FIG. 5) detecting radiation transmitted through the patient, is installed on the display device 40. In a case in which this control program is executed, an imaging condition setting screen, which receives the setting of imaging conditions, and the like, is displayed on the touch panel 41. Further, for example, imaging conditions, such as patient information and a region to be imaged, are set and input on the imaging condition setting screen, and the magnitude of a tube voltage to be applied to the radiation source 14 of the radiation generating device 10, the accumulation time of detection signals of a radiation detector 52 of the radiation detecting device 60, and the like are set according to the imaging conditions. The display device 40 outputs a control signal to the radiation generating device 10 and the radiation detecting device 60 according to the tube voltage of the radiation source 14 and the accumulation time of the radiation detector 52, and controls the to the radiation generating device 10 and the radiation detecting device 60. That is, the display device 40 of this embodiment also functions as a control device for the radiation generating device 10 and the radiation detecting device 60.

Figure 5:
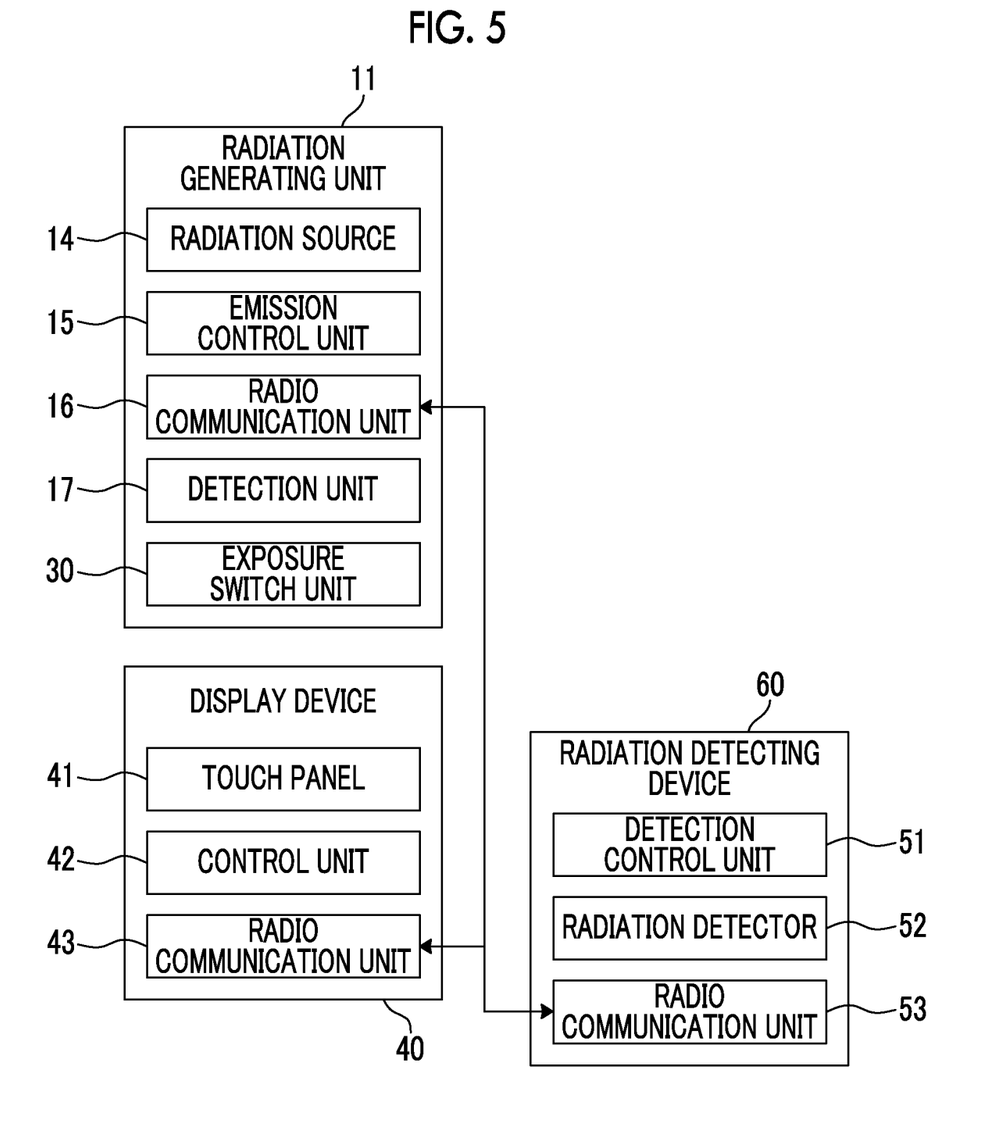
FIG. 5 is a block diagram showing the internal configuration of a radiation generating unit, a display device, and a radiation detecting device.

FIG. 5 is a block diagram showing the internal configuration of the radiation generating unit 11 of the radiation generating device 10, the display device 40, and the radiation detecting device 60. The above-mentioned radiation source 14, an emission control unit 15 that controls the emission of radiation, a radio communication unit 16, and a detection unit 17 are provided in the housing of the radiation generating unit 11.

The emission control unit 15 of the radiation generating unit 11 validly receives only the irradiation instruction for radiation of the exposure switch unit 30 between the irradiation instruction for radiation of the exposure switch unit 30 and the irradiation instruction for radiation of the exposure switch mark 50 displayed on the display device 40 in a case in which the display device 40 is installed on the radiation generating device 10. Conversely, the emission control unit 15 allows radiation to be emitted according to the exposure switch unit 30 being pressed, but does not allow radiation to be emitted from the radiation generating device 10 even though the exposure switch mark 50 displayed on the display device 40 is touched in a case in which the display device 40 is installed on the radiation generating device 10.

According to this structure, it is possible to prevent the emission of radiation that is caused in a case in which the exposure switch mark 50 displayed on the display device 40 is operated by mistake.

Further, the emission control unit 15 validly receives only the irradiation instruction for radiation of the exposure switch mark 50 between the irradiation instruction for radiation of the exposure switch unit 30 and the irradiation instruction for radiation of the exposure switch mark 50 displayed on the display device 40 in the case of a state in which the display device 40 is separated from the radiation generating device 10. Conversely, the emission control unit 15 allows radiation to be emitted according to the exposure switch mark 50 displayed on the display device 40 being touched, but does not allow radiation to be emitted from the radiation generating device 10 even though the exposure switch unit 30 is pressed in the case of a state in which the display device 40 is separated from the radiation generating device 10.

According to this structure, since a user can give an instruction to irradiate a subject with radiation by using the display device 40 at a position away from the radiation generating device 10, it is possible to reduce the amount of radiation to be applied to the user.

Further, the detection unit 17 detects the mounting/detachment of the display device 40 on/from the radiation generating device 10. Specifically, the detection unit 17 emits light to the outside through a hole 11*b* (see FIG. 4) that is formed on the back of the housing of the radiation generating unit 11, and receives the reflected light thereof. In a case in which the display device 40 is installed on the radiation generating device 10 and the reflected light reflected by the display device 40 is received by the detection unit 17, the installation of the display device 40 on the radiation generating device 10 is detected. On the contrary, in a case in which a state in which the reflected light reflected by the display device 40 is not received by the detection unit 17 is detected, the separation of the display device 40 from the radiation generating device 10 is detected.

The mounting/detachment of the display device 40 on/from the radiation generating device 10 is detected by an optical sensor in this embodiment, but the invention is not limited thereto. Proximity sensors, such as other magnetic force sensors, can be used. Further, a mechanical switch may be provided without the use of such a non-contact sensor to detect the mounting/detachment of the display device 40 on/from the radiation generating device 10.

The radio communication unit 16 communicates with a radio communication unit 43 of the display device 40 and a radio communication unit 53 of the radiation detecting device 60 by radio. In a case in which the exposure switch mark 50 of the display device 40 is touched, a detection signal for the exposure switch mark 50 being touched is transmitted from the radio communication unit 43 of the display device 40 and is received by the radio communication unit 16 of the radiation generating unit 11. Then, the emission control unit 15 allows the radiation generating unit 11 to emit radiation according to the reception of the detection signal that is performed by the radio communication unit 16.

Further, the radio communication unit 16 receives a control signal that is transmitted from the radio communication unit 43 of the display device 40. Then, the emission control unit 15 controls the tube voltage of the radiation source 14 and the like and controls the emission of radiation on the basis of the control signal that is received by the radio communication unit 16.

The display device 40 includes the above-mentioned touch panel 41, a control unit 42, and the radio communication unit 43. The control unit 42 controls the display of the touch panel 41 and controls the operations of the radiation generating device 10 and the radiation detecting device 60. A control signal for the radiation generating device 10 is transmitted from the radio communication unit 43 of the display device 40 as described above, and is received by the radio communication unit 16 of the radiation generating device 10. Further, a control signal for the radiation detecting device 60 is transmitted from the radio communication unit 43 of the display device 40, and is received by the radio communication unit 53 of the radiation detecting device 60.

The radiation detecting device 60 includes a detection control unit 51, the above-mentioned radiation detector 52, and the radio communication unit 53.

The radiation detector 52 detects radiation, which is emitted from the radiation generating device 10 and is transmitted through a patient, and outputs a detection signal of radiation. For example, a detector, which includes a scintillator (phosphor) for converting incident radiation into visible light and a thin-film-transistor (TFT) active matrix substrate, can be used as the radiation detector 52. The radiation detector 52 is not limited thereto, and a so-called direct-conversion radiation detector, which directly converts incident radiation into charge signals, may be used.

Figure 6:
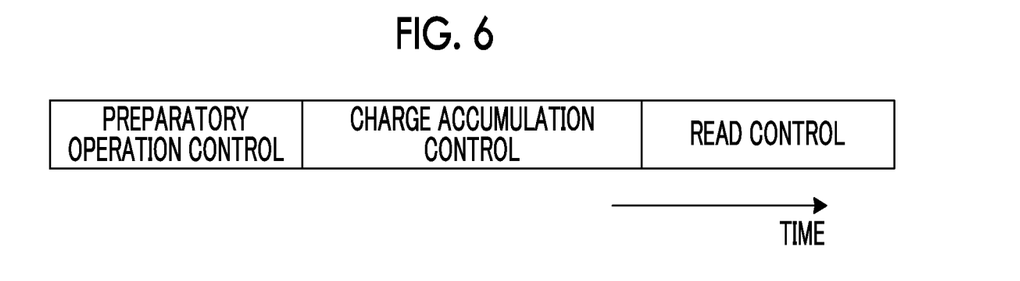
FIG. 6 is a diagram illustrating the operation control of a radiation detector.

The detection control unit 51 includes, for example, a central processing unit (CPU) and the like, and controls the operation of the radiation detector 52. Examples of the operation control of the radiation detector 52 include preparatory operation control, charge accumulation control, and read control as shown in FIG. 6.

In the period of the preparatory operation control of the radiation detector 52, a high voltage is applied to the radiation detector 52 and the radiation detector 52 is in a state in which the radiation detector 52 can detect radiation. A signal, which indicates the completion of a preparation operation, is transmitted to the radio communication unit 16 of the radiation generating unit 11 and the radio communication unit 43 of the display device 40 from the radio communication unit 53 of the radiation detecting device 60.

Further, in a case in which an instruction to start irradiation is received by the exposure switch unit 30 of the radiation generating unit 11 or the exposure switch mark 50 of the display device 40, radiation is emitted toward a patient from the radiation generating device 10 and an accumulation start control signal for a detection signal of radiation is output to the radio communication unit 53 of the radiation detecting device 60 from the radio communication unit 16 of the radiation generating unit 11 or the radio communication unit 43 of the display device 40 according to the emission of radiation.

The detection control unit 51 of the radiation detecting device 60 starts charge accumulation control from a time when the accumulation start control signal is received by the radio communication unit 53. Specifically, the detection control unit 51 controls the radiation detector 52 and allows charges, which are generated by the irradiation with the radiation transmitted through the patient, to be accumulated. The accumulation of the charges is performed at an accumulation time that is preset by the display device 40.

Then, the detection control unit 51 starts the read control from a time when a charge accumulation operation ends. Specifically, the detection control unit 51 controls the radiation detector 52 and starts to read the accumulated charge signals. A detection signal of radiation, which corresponds to the charge signal read from the radiation detector 52, is stored in a storage medium, such as a memory provided in the radiation detecting device 60. The detection signal of radiation, which is stored in the storage medium, is subjected to predetermined signal processing and is then output to the display device 40 from the radio communication unit 53. The detection signal of radiation is received by the radio communication unit 43 of the display device 40, and the control unit 42 of the display device 40 allows the touch panel 41 to display a radiation image on the basis of the received detection signal of radiation.

In the radiation-irradiation system 1 of the first embodiment, the emission control unit 15 does not allow radiation to be emitted even though the exposure switch mark 50 displayed on the display device 40 is touched in a case in which the display device 40 is installed on the radiation generating device 10. However, the emission control unit 15 may be made not to validly receive the irradiation instruction for radiation of the exposure switch mark 50 by not displaying the exposure switch mark 50 in a case in which the display device 40 is installed on the radiation generating device 10. That is, in the invention, making the irradiation instruction for radiation of the exposure switch mark 50 not be validly received also includes making the exposure switch mark 50 not be displayed.

Next, a second embodiment of the radiation-irradiation system of the invention will be described. In the radiation-irradiation system 1 of the first embodiment, the emission control unit 15 is adapted to validly receive only the irradiation instruction for radiation of the exposure switch unit 30 of the radiation generating device 10 in a case in which the display device 40 is installed on the radiation generating device 10, and is adapted to validly receive only the irradiation instruction for radiation of the exposure switch mark 50 displayed on the display device 40 in a case in which the display device 40 is separated from the radiation generating device 10. However, the radiation-irradiation system of the second embodiment is adapted so that the emission control unit 15 validly receives only the irradiation instruction for radiation of the exposure switch unit 30 of the radiation generating device 10 in a case in which the display device 40 is present in the range of a preset distance even though the display device 40 is separated from the radiation generating device 10. Conversely, the emission control unit 15 does not allow radiation to be emitted even though the exposure switch mark 50 of the display device 40 is touched in a case in which the display device 40 is present in the range of the preset distance even though the display device 40 is separated from the radiation generating device 10.

According to this structure, it is possible to prevent the emission of radiation that is caused in a case in which the exposure switch mark 50 displayed on the display device 40 is operated by mistake.

Further, the emission control unit 15 validly receives only the irradiation instruction for radiation of the exposure switch mark 50 displayed on the display device 40 in a case in which the display device 40 is present outside the range of the preset distance from the radiation generating device 10. Conversely, the emission control unit 15 does not allow radiation to be emitted even though the exposure switch unit 30 of the radiation generating device 10 is pressed in a case in which the display device 40 is present outside the range of the preset distance from the radiation generating device 10.

According to this structure, since a user can give an instruction to irradiate a subject with radiation by using the display device 40 at a position away from the radiation generating device 10, it is possible to reduce the amount of radiation to be applied to the user.

In the second embodiment, it is preferable that the above-mentioned preset distance is in the range of 2 m to 5 m. Further, as a method of measuring a distance between the display device 40 and the radiation generating device 10, for example, a signal for distance measurement may be transmitted to the radio communication unit 43 of the display device 40 from the radio communication unit 16 of the radiation generating device 10 and a response signal of the signal may be transmitted to the radio communication unit 16 of the radiation generating device 10 in a case in which the radio communication unit 43 of the display device 40 receives the signal for distance measurement. Then, the emission control unit 15 may measure a time that has passed until the response signal of the signal is received after the signal for distance measurement is transmitted, and may measure a distance between the display device 40 and the radiation generating device 10 from the measured time. The method of measuring a distance between the display device 40 and the radiation generating device 10 is not limited thereto, and, for example, a global positioning system (GPS) signal and the like may be used.

Furthermore, even in the radiation-irradiation system of the second embodiment, the emission control unit 15 may be made not to validly receive the irradiation instruction for radiation of the exposure switch mark 50 by not displaying the exposure switch mark 50 in a case in which the display device 40 is present in the range of the preset distance from the radiation generating device 10.

What is claimed is:

1. A radiation-irradiation system comprising:
a radiation generating device that includes a radiation source for generating radiation, an emission control unit for controlling emission of the radiation, and an exposure switch for receiving an irradiation instruction for generating radiation; and
a display device that includes a touch panel,
wherein the radiation generating device and the display device include radio communication units that communicate with each other by radio, respectively,
the display device is adapted to be detachably mounted on the radiation generating device, and displays an indicator, which receives an irradiation instruction for generating radiation, on the touch panel,
the emission control unit validly receives only the irradiation instruction for generating radiation of the exposure switch, between the irradiation instruction for generating radiation of the exposure switch and the irradiation instruction for generating radiation of the indicator displayed on the touch panel, in a case in which the display device is installed on the radiation generating device,
the emission control unit validly receives only the irradiation instruction for generating radiation of the indicator, between the irradiation instruction for generating radiation of the exposure switch and the irradiation instruction for generating radiation of the indicator displayed on the touch panel, in a case of a state in which the display device is separated from the radiation generating device, and
the touch panel of the display device displays the indicator in the case of the state in which the display device is separated from the radiation generating device, and does not display the indicator in the case in which the display device is installed on the radiation generating device.

2. The radiation-irradiation system according to claim 1, wherein the radio communication unit of the display device communicates with a radiation detector, which detects the radiation transmitted through a subject, by radio.

3. The radiation-irradiation system according to claim 1, wherein the display device is a tablet terminal.

4. The radiation-irradiation system according to claim 1, wherein the display device is adapted to be detachably mounted on a surface of the radiation generating device opposite to an emission side of the radiation.

5. The radiation-irradiation system according to claim 1, wherein the radiation-irradiation system is transportable.

6. The radiation-irradiation system according to claim 2, wherein the display device outputs an accumulation start control signal for a detection signal of the radiation to the radiation detector according to emission of radiation from the radiation generating device.

7. The radiation-irradiation system according to claim 4, wherein an installation member on which the display device is to be installed is provided on the surface of the radiation generating device opposite to an emission side of the radiation.

8. A radiation-irradiation system comprising:
a radiation generating device that includes a radiation source for generating radiation, an emission control unit for controlling emission of the radiation, and an exposure switch for receiving an irradiation instruction for generating radiation; and
a display device that includes a touch panel,
wherein the radiation generating device and the display device include radio communication units that communicate with each other by radio, respectively,
the display device is adapted to be detachably mounted on the radiation generating device, and displays an indicator, which receives an irradiation instruction for generating radiation, on the touch panel,
the emission control unit validly receives only the irradiation instruction for generating radiation of the exposure switch, between the irradiation instruction for generating radiation of the exposure switch and the irradiation instruction for generating radiation of the indicator displayed on the touch panel, in a case in which the display device is present in a range of a preset distance from the radiation generating device,
the emission control unit validly receives only the irradiation instruction for generating radiation of the indicator, between the irradiation instruction for generating radiation of the exposure switch and the irradiation instruction for generating radiation of the indicator displayed on the touch panel, in a case in which the display device is present outside the range of the preset distance from the radiation generating device, and
wherein the touch panel of the display device displays the indicator in the case in which the display device is present outside the range of the preset distance from the radiation generating device, and does not display the indicator in the case in which the display device is present in the range of the preset distance from the radiation generating device.

9. The radiation-irradiation system according to claim 8, wherein the radio communication unit of the display device communicates with a radiation detector, which detects the radiation transmitted through a subject, by radio.

10. The radiation-irradiation system according to claim 8, wherein the display device is a tablet terminal.

11. The radiation-irradiation system according to claim 8, wherein the display device is adapted to be detachably mounted on a surface of the radiation generating device opposite to an emission side of the radiation.

12. The radiation-irradiation system according to claim 8, wherein the radiation-irradiation system is transportable.

13. The radiation-irradiation system according to claim 9, wherein the display device outputs an accumulation start control signal for a detection signal of the radiation to the radiation detector according to emission of radiation from the radiation generating device.

14. The radiation-irradiation system according to claim 11, wherein an installation member on which the display device is to be installed is provided on the surface of the radiation generating device opposite to an emission side of the radiation.

* * * * *